US009128053B2

(12) United States Patent
Rosen et al.

(10) Patent No.: US 9,128,053 B2
(45) Date of Patent: Sep. 8, 2015

(54) PRECISION DENSITOMETER FOR RADIOSENSITIVE FILM

(71) Applicant: Wisconsin Alumni Research Foundation, Madison, WI (US)

(72) Inventors: Benjamin S. Rosen, Madison, WI (US); Keith A Kunugi, Madison, WI (US); Frank Grenzow, New Glarus, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/960,135

(22) Filed: Aug. 6, 2013

(65) Prior Publication Data

US 2015/0041668 A1    Feb. 12, 2015

(51) Int. Cl.
*G01N 21/59* (2006.01)
*G01J 1/42* (2006.01)
*G01T 1/00* (2006.01)

(52) U.S. Cl.
CPC ............... *G01N 21/5911* (2013.01); *G01J 1/42* (2013.01); *G01T 1/00* (2013.01)

(58) Field of Classification Search
USPC ......................................................... 250/395
See application file for complete search history.

(56) References Cited

U.S. PATENT DOCUMENTS

| | | | | |
|---|---|---|---|---|
| 3,839,634 A | * | 10/1974 | Buchmann | 250/214 VT |
| 5,172,419 A | * | 12/1992 | Manian | 382/132 |
| 2003/0136894 A1 | * | 7/2003 | Gerlach | 250/201.1 |
| 2004/0008347 A1 | * | 1/2004 | Kwok et al. | 356/331 |

OTHER PUBLICATIONS

Niroomand-Rad et al. "Radiochromic film dosimetry: Recommendations of AAPM Radiation Therapy Committee Task Group 55", Mediacl Physics vol. 25, No. 11, pp. 2093-2115, Nov. 1998.*

* cited by examiner

*Primary Examiner* — David Porta
*Assistant Examiner* — Meenakshi Sahu
(74) *Attorney, Agent, or Firm* — Boyle Fredrickson, S.C.

(57) ABSTRACT

A precision densitometer for radiosensitive films and the like provides point-to-point scanning in which a laser source and collimated receiver are moved in tandem over the area of the film. The film may be supported only at its edges to remove scattering and interference caused by a glass support bed. Highly repeatable 25 μm resolution density measurements may be obtained.

20 Claims, 3 Drawing Sheets

PRECISION DENSITOMETER FOR RADIOSENSITIVE FILM

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to an optical densitometer for determining the density of radiosensitive films and in particular to a densitometer providing improved resolution and accuracy.

Radiosensitive films are used for radiation dose measurement, for example, in medical radiotherapy in which ionizing radiation is used to treat malignant cells in cancer or the like. Such films, which provide high spatial resolution, are particularly useful in advanced radiation therapy systems, such as intensity modulated radiation therapy (IMRT) in which complex, fine beam patterns must be measured. Generally, the films are sensitive to ionizing radiation and can provide a spatial resolution as little as 25 micrometers and a wide dynamic range from a few milliGray to greater than 40 Gray.

Radiochromic films are radiosensitive films that change color on exposure to ionizing radiation without the need for chemical or other processing. While such films can be used for qualitative dose measurement, normally they are scanned, for example, with a flatbed optical scanning mechanism and the measured film density, that is light absorption caused by the exposed film pigment, is applied to a calibration curve to yield a quantitative measurement of received radiation dose. The resulting scans may be further processed, for example, to extract isodose curves or other quantitative information.

While radiosensitive films provide advantages over ionization detectors and solid-state detectors in terms of spatial resolution and dynamic range, obtaining consistent quantitative results with radiosensitive films can be difficult.

SUMMARY OF THE INVENTION

The present inventors have identified a number of significant sources of inaccuracy in the quantitative scanning of radiosensitive films, including scattering from off-axis, incident light from broad area illumination, internal scattering within the charge-coupled device light sensors, and scattering and interference effects introduced by the supporting glass bed. In addition, the inventors have noted that the characteristics of the film's emulsion are changed by scanning-induced heating of the film and additional variations may be introduced by spectral mis-match between the light source illuminating the film and the particular film chemistry.

The present invention addresses these issues of scattering and interference by providing a "point-to-point" scanning mechanism operating on the film as it is suspended in free space. The point-to-point scan uses a moving point light source and point detector to largely eliminate scatter from off-axis light and scatter within a sensor array. Suspension of the film eliminates the scattering and interference from the glass bed. By moving the light source and detector, consistent illumination and detection is obtained over the entire scan area, reducing sensitivity in the results to film placement and orientation. Focused and hence more efficient illumination together with cooling significantly reduces changes in the emulsion caused by heating. In some embodiments a variable wavelength or dual wavelength laser source may be used to accommodate film chemistry variations and to provide improved calibration density measurements of the film to radiation dose.

Specifically, the present invention provides a film densitometer having a film support holding a film along a scanning plane. A scanning mechanism supports a light source and a light detector so that the light source and light detector remain aligned along a common axis substantially perpendicular to a scanning plane on opposite sides of the scanning plane while the scanning mechanism moves the light source and a light over the film according to electrical movement signals. A controller generates movement signals to move the light source and light detector among a set of different locations on each side of a film as held in the support while illuminating the film with the light source and to detect transmitted light through the film at the set of different locations with the light detector to provide a detection signal at each location. A set of density values based on the detection signal are then output for the locations. The light source may be a laser emitting a focused beam along the common axis and the light detector may be a photo detector selectively receiving light primarily along the common axis.

It is thus a feature of at least one embodiment of the invention to reduce measurement variations related to film position and orientation in the scanner. By moving the light source and detector over an area as opposed to providing broad area illumination or broad area detection, more uniform detection fields may be implemented.

The laser may provide a substantially circular illumination spot on the film as held in the support, for example, less than 100 μm in diameter.

It is a feature of at least one embodiment of the invention to greatly reduce scatter from off-axis incident illumination by illuminating only on the portion of the film being measured.

Similarly, the light detector may provide a substantially circular field of view on the film of less than 100 μm in diameter, for example, by focusing or collimation.

It is a feature of at least one embodiment of the invention to further reduce scattering by blocking off-axis light scattered by the film itself.

The controller may apply a calibration function to the detection signals to provide the density values representing radiation dose.

It is thus a feature of at least one embodiment of the invention to provide a quantitative dose measurement suitable for quality assurance or calibration of radiation equipment where high-resolution measurement must be obtained.

The output can provide one or more of an image representing density values as image pixels having values corresponding to the detection signals and coordinates corresponding to the different locations and isodose curves of the density values.

It is thus a feature of at least one embodiment of the invention to provide for standard output measurements familiar to those measuring radiation dose.

The scanning mechanism may include motors for moving the light source and light detector in two perpendicular directions and position sensors providing position signals indicating position of the light source and light detector in the two perpendicular directions, and the scanning mechanism may provide a feedback control of the motors according to a difference between the position signals and the electrical movement signals.

It is thus a feature of at least one embodiment of the invention to provide a mechanism that allows point-to-point measurement at high throughput speeds with sufficient accuracy.

The laser may have a wavelength substantially equal to 635 nm.

It is thus a feature of at least one embodiment of the invention to provide an illumination source well adapted for radiochromic films.

The laser may provide an output wavelength according to a control signal and the controller may execute the stored program to adjust the output wavelength of the laser according to a characteristic of a film held in the support.

It is thus a feature of at least one embodiment of the invention to permit tuning of the laser for maximum sensitivity of measurement, for example, at a peak sensitivity range of the film.

The laser may provide for at least two output was (for example using a single or multiple lasing elements) according to a control signal and the controller may execute the stored program to change the output wavelength of the laser at each of the set of locations to provide for detection signals for each of at least two wavelengths.

It is thus a feature of at least one embodiment of the invention to provide for multiple wavelength dimensions in the measurement process such as allows improved calibration of density to dose.

The light detector may be a photo diode.

It is thus a feature of at least one embodiment of the invention to eliminate internal scattering present in CCD and similar array devices.

The light detector may be collimated along the axis by a collimation aperture.

It is thus a feature of at least one embodiment of the invention to provide a simple method of controlling a field of view of the light detector that rejects off-axis light.

The scanning mechanism may provide at least one tray element supporting the film at edges of the film so that a center of the film is removed from contact with any support material.

It is thus a feature of at least one object of the invention to eliminate refraction and scattering that occur in glass support beds often used to support radiosensitive film for scanning.

The densitometer may include a light-opaque housing surrounding the scanning mechanism to block light external to the opaque shroud from the light detector.

It is thus a feature of at least one embodiment of the invention to eliminate the effect of variations in external light sources in the measurement of density.

The housing may include air-cooling elements for controlling a temperature within the housing to a substantially constant temperature.

It is thus a feature of at least one embodiment of the invention to eliminate or reduce effects of varying temperature and heating by the scanner itself in changing the measured density of the film.

These particular features and advantages may apply to only some embodiments falling within the claims and thus do not define the scope of the invention.

DETAILED DESCRIPTION OF THE PREFERRED EMBODIMENT

Figure 1:
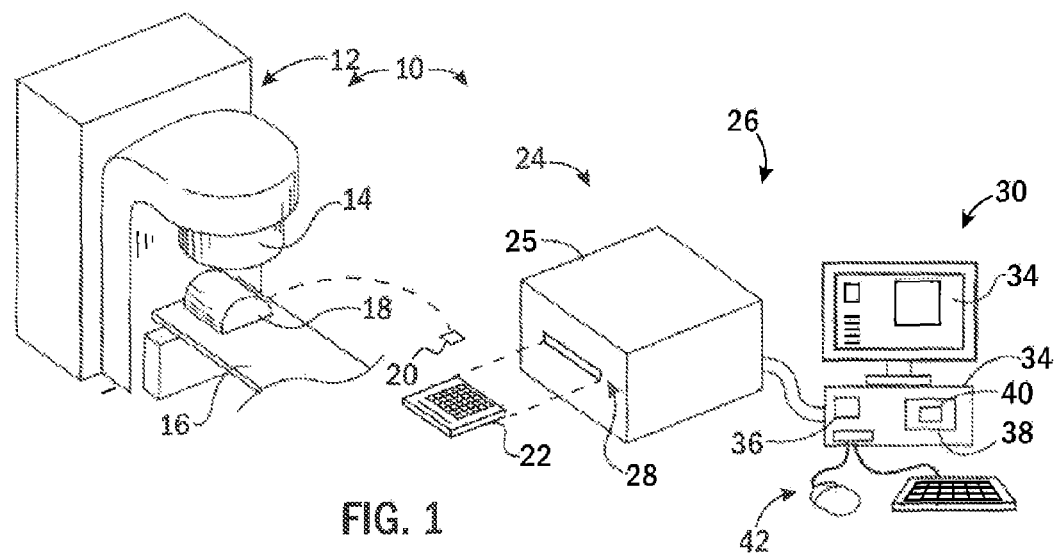
FIG. 1 is a simplified perspective representation of a radiotherapy suite showing an example radiotherapy machine exposing radiochromic film in a phantom and showing a densitometer according to the present invention having a tray for receiving the film and insertion into a housing for scanning, the densitometer including a computer for processing the scanned data.

Referring now to FIG. 1, a radiotherapy treatment suite 10, in which the present invention may be beneficially employed, may provide for a radiation therapy machine 12 having a radiation head 14 directing radiation toward a patient table 16. The radiation therapy machine 12 may, for example, be an intensity modulated radiation therapy machine (IMRT) such as a Tomotherapy® radiotherapy system manufactured by Accuray or the like providing complex modulated radiation beams at a plurality of angles. A radiation phantom 18 may be positioned on the table 16, for example, for quality assurance or calibration of the radiation therapy machine 12. The radiation phantom 18 may provide a structure that mimics tissue of a similarly situated human patient, for example, using a water equivalent plastic such as Lucite™.

Radiation received by the phantom 18 may be monitored through a set of radiosensitive film elements 20 inserted into the phantom 18, for example, comprised of squares of radiochromic film such as GAFCHROMIC® EBT radiochromic film.

After removal from the phantom 18, the film elements 20 may be arranged on a tray 22 subsequently inserted into scanner 24 of a densitometer 26. Generally the scanner 24 provides a light-opaque housing 25 shielding internal elements of the scanner (as will be described below) from external light. The housing 25 may be constructed from black ABS plastic, for example. The tray 22 may be installed through a slot 28 in the housing 25, the slot minimizing the admission of light from external sources into the housing 25 where that light may interfere with the densitometry measurements.

The scanner 24 may communicate with a standard desktop computer 30, for example, providing a graphic display 32 associated with a processing unit 34 including one or more computer processors 36 and associated computer memory 38. The computer memory 38, as is understood in the art, may hold a stored program 40 implementing various features of the present invention as will be described below. The processing unit 34 may further communicate with user input elements 42, for example a mouse and keyboard, according to techniques well understood in the art.

Figure 2:
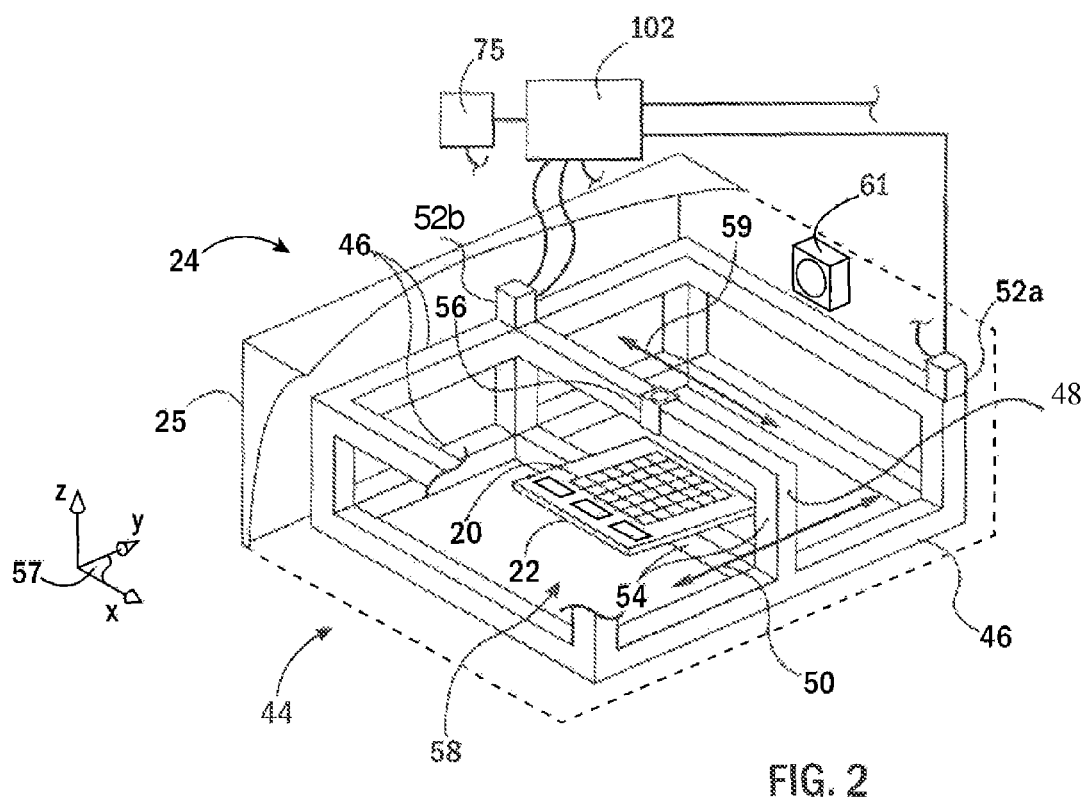
FIG. 2 is a perspective partial phantom view of the housing of the densitometer of FIG. 1 showing an internal scanning mechanism and the positioning of the tray along a scanning plane between a movable light source and detector (the latter not visible in FIG. 2)

Referring now to FIG. 2, the scanner 24 holds an x-y carriage 44 having lateral rails 46 on which a moving frame 48 may slide as driven by motor 52a to move in translation along a y-axis as indicated by arrow 50. The moving frame 48 in turn provides upper and lower transverse rails 54 that may hold, respectively, a light source 56 and light detector 58 (not visible in FIG. 2) above and below the scanning tray 22 when the scanning tray 22 is positioned generally horizontally within the scanner 24 to extend along a scanning plane 57.

The moving frame 48 holds a motor 52b moving the light source 56 and light detector 58 in unison in a direction parallel to an x-axis as indicated by arrow 59. Motors 52 may, for example, be STM NEMA 17 form factors.

The housing 25 may include one or more cooling fans 61, for example, thermostatically controlled to maintain a constant temperature within the housing 25 against heating of the air inside the housing 25 by the motors 52 and the light source 56.

Figure 3:
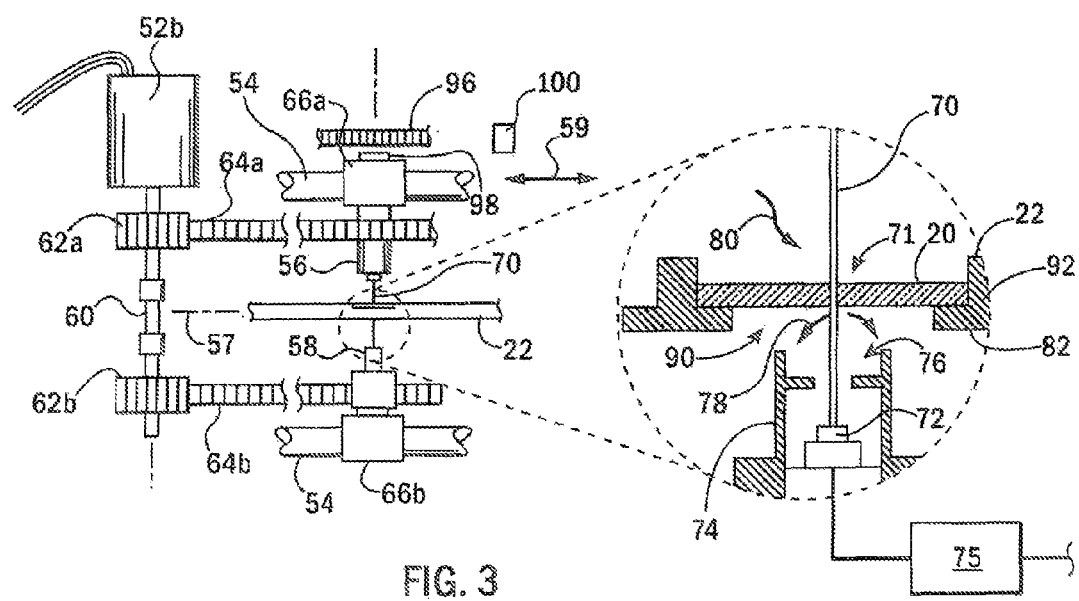
FIG. 3 is a fragmentary side elevational view and expanded detail of the light source, detector and tray of FIG. 2.

Referring now also to FIG. 3, motor 52b may provide a torque tube 60 extending generally vertically downward from the motor 52b as depicted and attached to two co-rotating timing belt pulleys 62a and 62b. The timing belt pulleys 62a and 62b communicate through timing belts 64a and 64b extending along the x-axis, respectively, to attach to carriage slides 66a and 66b, the latter movable along respective transverse rails 54 in the x-direction.

Carriage slide 66a supports light source 56 which may be a laser directing a focused beam 70 downward to the tray 22 along axis 81 and generally perpendicular to the scanning plane 57 in parallel to the z-axis. The beam 70 is focused in a circular spot 71 on a surface of the film element 20 held in the tray 22. The light passes through the film element 20 to be received by the light detector 58. A suitable laser for one embodiment of the invention is the Edmund Optics LDM 635 nm laser diode.

The illuminated spot 71 on the film element 20 will typically be a circular focal point of less than 50 μm in diameter and desirably as little as 25 μm in diameter.

Light detector 58 may be an upwardly exposed photodiode 72 (for example of a type commercially available from Hamamatsu) and may be encased in a collimating housing 74 having an aperture 76 that generally rejects off-axis, scattered light 78 from the laser beam 70 as scattered by the film element 20 and deviating from axis 81. Aperture 76 is preferably sized to be approximately the size of a focal spot of the beam 70 on the film element 20. Ambient light 80 is generally reduced or eliminated by the opaque housing 25 discussed above and rejected to the extent that it is also off-axis.

The signal from the photodiode may be received by a pre-processing circuit 75 including a logarithmic amplifier (MAXIM4206KIT) applying a logarithm to the received signal and then converting the received signal into a digital word by a 12-bit analog-to-digital converter (Keithley KUSB-3100). The digital word may be communicated to the processing unit 34 for processing as will be described.

It will be understood that the stiffness of the torque tube 60 provides unison motion of the carriage slides 66a and 66b so that the light source 56 and light detector 58 remain substantially aligned along the common axis 81 with transverse movement as indicated by arrow 59. The light source 56 and light detector 58 may be moved in this alignment over the entire area of the tray 22 in a raster scan through successive or simultaneous movement along the x- and y-axes through motors 52a and 52b while maintaining alignment above and below the tray 22 along the axis 81.

Figure 6:
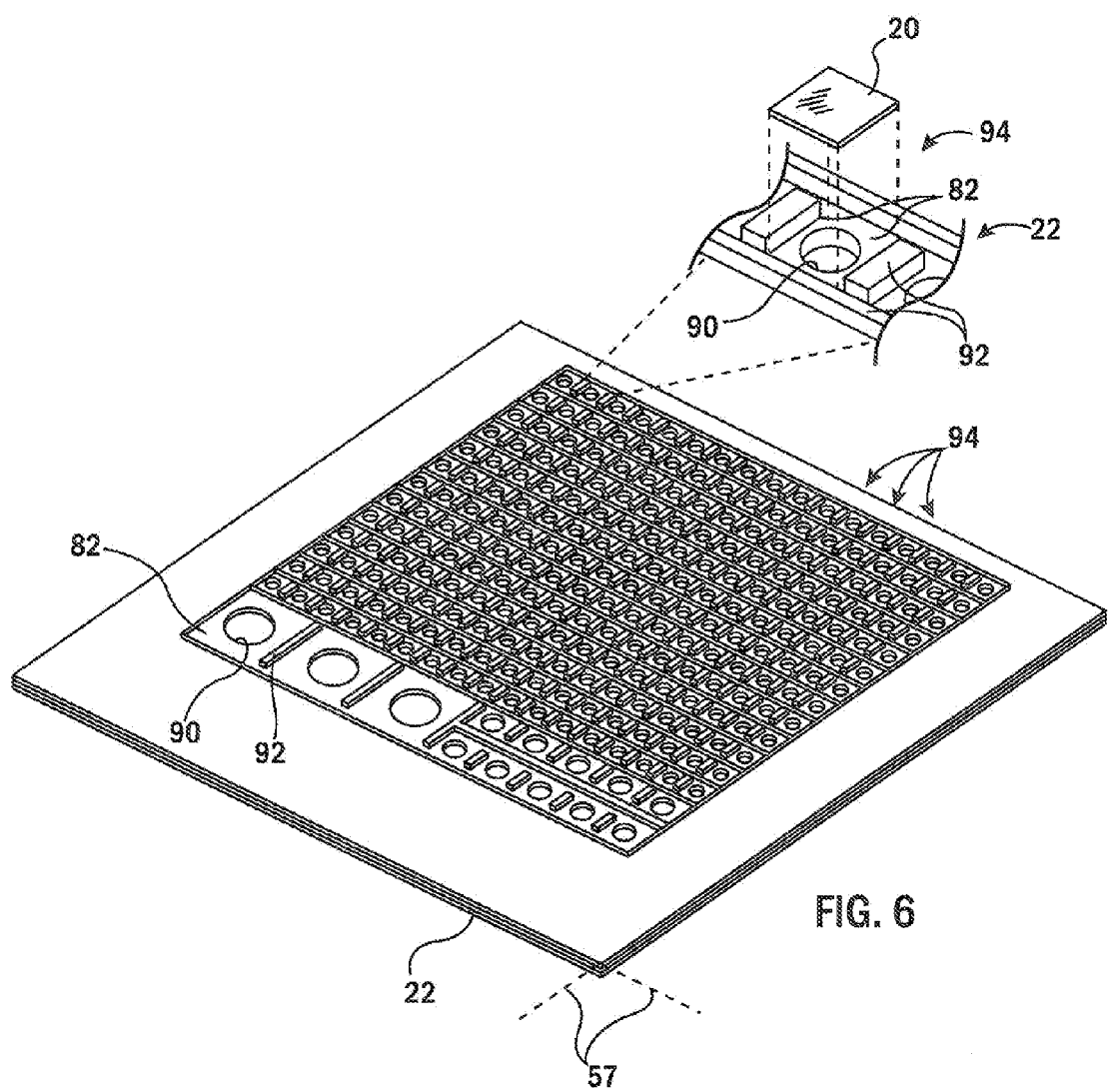
FIG. 6 is a perspective view and enlarged fragmentary view of the tray of FIG. 1.

Referring to FIGS. 3 and 6, the film element 20 as held in the tray 22 is supported substantially only at its edges by frame lips 82 as centered over a central aperture 90 by frame walls 92 which together with the frame lips 82 and aperture 90 provide a pocket 94 for receiving one film element 20. In this way, a center region of the film element 20, being a region of interest for densitometry, is removed from any supporting structure that might cause aberration scattering or distortions as may occur with the supporting glass bed in a standard flatbed scanner.

Multiple pockets 94 may be tiled over the surface of the tray 22 and may be given different dimensions for holding different sizes of film elements 20. The tray 22 may be generally supported at its edges away from the pockets 94 on a pair of slide rails or a conveyor mechanism (not shown) of the type well known in the art.

Referring again to FIGS. 2 and 3, a linear position marker 96, for example a periodically magnetized strip of material, may extend along at least one of each of the rails 46 and 54 to be sensed by a corresponding sensor reader 98, for example a magnetic pickup head, to provide precise relative position sensing of at least one of carriage slides 66a and 66b in the transverse direction and of the moving frame 48 in the longitudinal direction. The position marker 96 and sensor reader 98 may be coupled with limit switches 100 which provide absolute reference positions of the carriage slides 66a or 66b and moving frame 48 so that absolute position may be derived (for example by homing the carriage slides 66a or 66b or moving frame 48 against the limit switches 100). Signals from each of the sensor readers 98 are received by a feedback controller 102 conveniently positioned within the housing 25 but alternatively implemented by the processing unit 34 which may control motors 52a and 52b to provide for 25 μm accurate positioning in the x-y plane. As is understood in the art, the feedback controller accepts a motion command and compares that to a sensed position to produce an error value that is used to drive the motors 52. The accuracy of such a feedback system is limited only by the accuracy of the position sensor (linear position marker 96 and sensor reader 98) which may be 25 μm in one embodiment.

Figure 4:
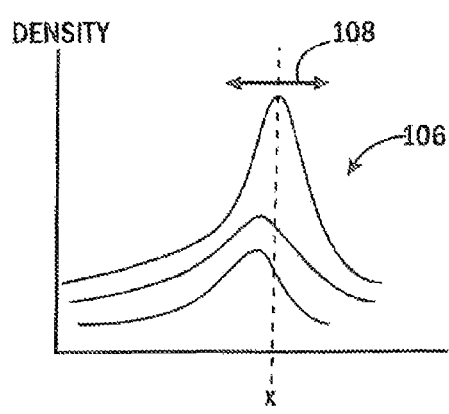
FIG. 4 is a set of simplified calibration curves for radiochromic film plotting density versus wavelength for different radiation exposure levels.

Referring now to FIGS. 3 and 4, the program 40 of the processing unit 34 may hold a set of calibration curves 106, each curve associated with a different radiation dose level, and each curve describing a density of the film element 20 in different wavelength bands (lambda) when the film is exposed to the associated dose level. The calibration curves 106 may be used to convert received signals from the scanner 24 indicating density into a quantitative dose value indicating radiation dose. In one embodiment, the light source 56 may be a tunable laser whose wavelength (lambda) may be adjusted as indicated by arrow 108 to provide for a wavelength maximum density sensitivity, for example, as indicated aligned with peaks in each of the curves 106. One suitable laser wavelength may be 635 nm.

During operation of the scanner 24, processing unit 34 will operate as a controller to move the axis 81, for example, in a raster scan pattern over the area of the tray 22. At regular intervals, for example 25 μm intervals, a signal from the light detector 58 may be acquired, for example, by the 12 bit A/D converter, and stored together with position coordinates of the axis 81 in the x-y plane. By moving the light source 56 and light detector 58, uniformity of measurement can be ensured over an entire area of the scan largely eliminating the variations which occur when an area illuminator is used for this purpose. Reducing the focal spot area greatly reduces the off-axis, scattered light 78 both from the detected region and regions outside of the detected region. Upon completion of the scan, the density values may be converted to dose values and an output provided, for example, on the display 32.

Figure 5:
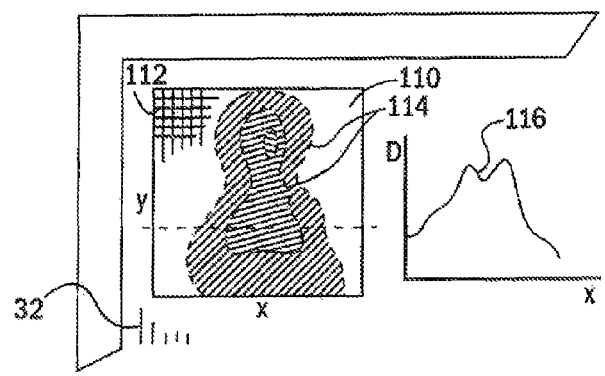
FIG. 5 is an example output of the densitometer of FIG. 1 as displayed on the computer screen showing a density image, isodose curves, and a quantitative longitudinal plot.

Referring now to FIG. 5, generally the display will provide an image 110 having multiple pixels 112 whose color or gray value will be proportional to a calculated dose at a location in the scan corresponding to the coordinates of the pixel 112. Thus an image is formed that looks substantially like the film element 20. Because each pixel 112 is associated with a numeric value, isodose lines 114 may be calculated and superimposed on the image 110 according to techniques well known in the art. In addition quantitative values 116, for example, displayed as the vertical axis of a plot dose along a given transverse slice (x-axis) through the image 110 may be provided for precise understanding of dose levels. It will be appreciated that other standard manipulations of this information may be provided including average dose within a predetermined area determining peak dose and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "controller" "processor" "circuit" can be understood to include one or more such devices that can communicate in a stand-alone and/or a distributed environment(s), and can thus be configured to communicate via wired or wireless communications with other processors, where such one or more processor can be configured to operate on one or more processor-controlled devices that can be similar or different devices. That is to say, unless specifically noted, the location of these devices and how the functionality is distributed is not critical. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A film densitometer comprising:
   a film support adapted to hold a radiosensitive film extending along a scanning plane;
   a light source;
   a light detector;
   a housing having an aperture sized to allow light rays along a common axis substantially perpendicular to the scanning plane to pass through the aperture and rejecting substantially off-axis light rays from passing through the aperture;
   a scanning mechanism movably supporting the light source, the housing and the light detector so that the light source, the housing, and the light detector remain aligned along the common axis substantially perpendicular to the scanning plane, the light source on an opposite side of the scanning plane from the housing and light detector, and the scanning mechanism moving the light source and a light with respect to the support over an area of the support according to received electrical movement signals wherein the scanning mechanism provides at least one tray element supporting the film at edges of the film so that a center of the film is removed from contact with any support material; and
   a controller communicating with the scanning mechanism and executing a stored program to:
   (1) generate electrical movement signals to move the light source, the housing, and the light detector among a set of different locations on respective sides of a film as held in the support while illuminating the film with the light source;
   (2) detect transmitted light through the film at the set of different locations with the light detector to provide a detection signal at each location; and
   (3) output scan data providing a set of density values and associated locations based on the detection signal at multiple locations;
   wherein the light source is a laser emitting a focused laser beam along the common axis and the light detector is a photo detector selectively receiving light primarily along the common axis; and
   wherein the aperture of the housing, is sized to approximate a size of a focal spot of the focused laser beam on the radiosensitive film.

2. The film densitometer of claim 1 wherein the laser provides a substantially circular illumination spot on the film as held in the support.

3. The film densitometer of claim 2 wherein the illumination spot is less than 100 μm in diameter.

4. The film densitometer of claim 1 wherein the light detector provides a substantially circular field of view on the film as held in the support.

5. The film densitometer of claim 4 wherein the field of view is less than 10 μm in diameter.

6. The film densitometer of claim 1 wherein the light source and light detector operate to provide a density resolution of the film of substantially no more than 25 μm.

7. The film densitometer of claim 1 wherein the density values are quantitative representations of radiation dose values at the different locations and the controller further executes the stored program to apply a calibration function to the detection signals to provide the density values.

8. The film densitometer of claim 7 wherein the output scan data provides an image representing density values as image pixels having values corresponding to the detection signals and coordinates corresponding to the different locations.

9. The film densitometer of claim 7 wherein the output scan data provides isodose curves.

10. The film densitometer of claim 1 wherein the scanning mechanism includes motors for moving the light source and light detector in two perpendicular directions and sensors providing position signals indicating position of the light source and light detector in the two perpendicular directions and wherein the scanning mechanism provides a feedback control of the motors according to a difference between the position signals and the electrical movement signals.

11. The film densitometer of claim 1 wherein the laser wavelength is substantially equal to 635 nm.

12. The film densitometer of claim 1 wherein the laser provides an output wavelength according to a control signal and wherein the controller executes the stored program to adjust the output wavelength of the laser according to a characteristic of a film held in the support.

13. The film densitometer of claim 1 wherein the laser provides for at least two output wavelengths according to a control signal and wherein the controller executes the stored program to change the output wavelength of the laser at each of the set of locations to provide for detection signals for each of at least two wavelengths.

14. The film densitometer of claim 1 wherein the light detector is a photo diode.

15. The film densitometer of claim 1 wherein the light detector is collimated along the axis by a collimation aperture.

16. The film densitometer of claim 1 wherein the film support provides multiple tray elements for holding multiple films within the scanning plane.

17. The film densitometer of claim 1 further including a light-opaque housing surrounding the scanning mechanism to block light external to the light-opaque housing from the light detector.

18. The film densitometer of claim 1 wherein the light-opaque housing includes air cooling elements for controlling a temperature within the housing to a substantially constant temperature.

19. A method of measuring radiation dose using a densitometer having:
   a film support adapted to hold a film extending along a scanning plane;
   a light source;
   a light detector;
   a housing having an aperture sized to allow light rays along a common axis substantially perpendicular to the scanning plane to pass through the aperture and rejecting substantially off-axis light rays from passing through the aperture;
   a scanning mechanism movably supporting the light source, the housing, and the light detector so that the light source, the housing, and the light detector remain aligned along the common axis substantially perpendicular to the scanning plane, the light source on an opposite side of the scanning plane from the housing and light detector, and the scanning mechanism moving the light source and a light with respect to the support over an area of the support according to received electrical movement signals; and
   a controller communicating with the scanning mechanism and executing a stored program to:
   generate electrical movement signals to move the light source, the housing, and the light detector among a set of different locations on each side of a film as held in the support while illuminating the film with the light source;
   detect transmitted light through the film at the set of different locations with the light detector to provide a detection signal at each location; and
   execute a stored program to (1) apply a calibration function to the detection signal to provide a set of density values and associated locations based on the detection signal at multiple locations wherein the density values are quantitative representations of radiation dose values at the different locations and (2) take at least one of an average radiation dose within a predetermined location area and a peak dose;
   wherein the light source is a laser emitting a focused laser beam along the common axis and the light detector is a photo detector selectively receiving light primarily along the common axis and wherein the aperture of the housing is sized to approximate a size of a focal spot of the focused laser beam on the radiosensitive film;
the method comprising the steps of
   (1) placing a radiosensitive film at a known position in a radiation therapy machine to be exposed according to a radiation treatment plan; and
   (2) placing the film in the film support of the densitometer to provide an output set of density values indicating radiation dose.

20. The method of claim 19 wherein the radiosensitive film is a radiochromic film.

* * * * *